US005658790A

United States Patent [19]
Gautsch

[11] Patent Number: 5,658,790
[45] Date of Patent: Aug. 19, 1997

[54] CELL CULTURE MEDIA FORMULATED IN UNIT DOSE

[75] Inventor: James W. Gautsch, Solana Beach, Calif.

[73] Assignee: Bio 101, Inc., Vista, Calif.

[21] Appl. No.: 591,885

[22] Filed: Jan. 25, 1996

Related U.S. Application Data

[60] Continuation-in-part of Ser. No. 309,926, Sep. 21, 1994, abandoned, which is a division of Ser. No. 962,418, Oct. 16, 1992, abandoned, which is a continuation-in-part of Ser. No. 267,530, Nov. 4, 1988, abandoned, which is a continuation-in-part of Ser. No. 903,481, Sep. 4, 1986, abandoned.

[51] Int. Cl.$^6$ .................... C12N 5/00; C12N 5/02
[52] U.S. Cl. ............ 435/404; 424/451; 435/253.6; 435/810; 436/808; 536/25.4; 536/25.41; 935/77; 935/78
[58] Field of Search .................. 435/240.31, 240.3, 435/253.6, 810; 436/808; 536/25.4, 25.41; 935/77, 78; 424/451

[56] References Cited

U.S. PATENT DOCUMENTS

| | | | |
|---|---|---|---|
| 3,625,833 | 12/1971 | Schaffer | 435/170 |
| 4,071,412 | 1/1978 | Eisenberg | 435/253.6 |
| 4,382,028 | 5/1983 | Paget | 435/71.2 |
| 4,544,637 | 10/1985 | Keggins et al. | 435/253.6 |
| 4,929,546 | 5/1990 | Mayra-Makinen | 435/253.04 |
| 5,089,413 | 2/1992 | Nelson et al. | 435/254.1 |
| 5,100,789 | 3/1992 | Yamashita | 435/136 |
| 5,108,701 | 4/1992 | Zakaria et al. | 422/21 |
| 5,137,812 | 8/1992 | Matner | 435/38 |
| 5,219,753 | 6/1993 | Borka et al. | 435/252.3 |
| 5,308,835 | 5/1994 | Clements | 514/12 |

OTHER PUBLICATIONS

Sigma Catalogue Feb. 1985 pp. 970–971 Sigma Chemical Comp. PO Box 14508 St. Louis MO 63178.

*Primary Examiner*—Herbert J. Lilling
*Attorney, Agent, or Firm*—Thomas Fitting

[57] ABSTRACT

The present invention contemplates a system and formulations for preparing cell culture medium useful for growing cells for the purpose of producing and isolating nucleic acids. Dry-concentrate culture medium compositions are described as packaged in unit dose form such as in dissolvable capsules.

18 Claims, No Drawings

5,658,790

1

CELL CULTURE MEDIA FORMULATED IN UNIT DOSE

CROSS REFERENCE TO RELATED APPLICATIONS

This is a continuation-in-part of application Ser. No. 08/309,926 filed Sep. 21, 1994, now abandoned, which is a division of application Ser. No. 07/962,418, filed Oct. 16, 1992, now abandoned, which is a continuation-in-part of application Ser. No. 07/267,530, filed Nov. 4, 1988, now abandoned, which is a continuation-in-part of application Ser. No. 06/903,481, filed Sep. 4, 1986, now abandoned, the disclosures of which are hereby incorporated herein by reference.

TECHNICAL FIELD

The present invention relates to cell culture media. More particularly, this invention contemplates systems and formulations for preparation of culture medium in unit dose form for supporting growth of cells containing plasmid DNA.

BACKGROUND

The isolation of preparative amounts of biologically active nucleic acid molecules remains an important aspect of molecular biology. This is especially the case with regard to isolation of DNA for use in recombinant methodologies where it is required to be in sufficiently pure form to be digestible by restriction endonucleases, to be a good substrate for polymerases and topoisomerases, and to be suitable for use as a transfection or transformation agent.

Over the years, many methods have been developed to isolate nucleic acid molecules which typically require the preparation of cultures of cells having the desired nucleic acid or plasmid. However, the methods for preparing culture medium are typically tedious, involving the weighing and mixing of numerous different ingredients, take extended periods of time to accomplish, require the processing of volumes of materials and often give variable results.

To date, the art has applied several different technologies to the problem of preparing convenient amounts of culture medium for growth of cells containing plasmid none of which have satisfactorily addressed the problems identified above.

From the foregoing it can be seen that there has been a long felt need by those practicing recombinant DNA technology for a reliable, rapid method for conveniently preparing a reproducibly uniform cell culture medium.

BRIEF SUMMARY OF THE INVENTION

The present invention contemplates systems and formulations for preparing cell culture medium useful for growing cells for the purpose of producing and isolating nucleic acids. The systems and methods take advantage of solutions to the problems, discovered by the inventor, of inconvenience of preparation and heterogeneity of formulation of cell culture medium.

In addition, the novel systems approach described herein permits a significant reduction in the level of skill and time required to produce medium for use in growing cells.

The invention describes a dry-concentrate culture medium composition packaged in unit dose form comprising an amount of cell culture medium in dry-concentrate form sufficient to prepare a preselected amount of culture medium. Preferably, the unit dose packaging is in the form of a capsule containing the dry culture medium. In a related embodiment, the packaging is comprised of a dissolvable material.

DETAILED DESCRIPTION OF THE INVENTION

A. Systems For Producing Cell Culture Medium

The present invention contemplates a system and formulation, in kit form, containing a dry-concentrate culture medium composition packaged in unit dose form useful for growing preselected amounts of cells containing plasmid DNA molecules. Typical cells are *E. coli* bacterial cells.

In one embodiment, the invention contemplates a system for medium preparation that includes, in a package, a unit dose of a dry-concentrate of a culture medium capable of supporting growth of cells containing plasmid DNA. A dry concentrate of medium comprises the dry reagent components that make up a conventional growth medium, such as LB-broth and the like bacterial culture medium. Exemplary media are described herein.

The term "unit dose" as it pertains to the medium of the present invention refers to physically discrete units each suitable for providing, upon dissolution in a predetermined amount of water, typically about 10 to about 500 ml, preferably 10 ml, 25 ml, 50 ml, 100 ml, 150 ml, 200 ml and the like, a complete culture medium capable of supporting the growth of cells containing plasmid DNA. The specifications for the novel unit dose of a medium of this invention are dictated by and are directly dependent on (a) the unique characteristics of the nutrients and the particular nutrient requirements of the organism to be grown, and (b) the limitations inherent in the art of compounding such nutrients for use in culture medium, as are disclosed in detail herein, these being features of the present invention.

The unit dose of dry-concentrate medium can be supplied in a variety of formats, including packaged in containers, pressed into tablets, and the like. Particularly preferred are gelatin capsule containers for ease of manipulation and ease of uniform dissolution of the concentrated medium.

The packaging for a unit dose form can vary widely. In one embodiment, the packaging is comprised of a dissolvable material, which can be either inert, inactive or nutritional, from the perspective of the nutrient medium the packaging contains. Preferably, the material is dissolvable in water or other aqueous solutions. The art of dissolvable packaging is well known and will not be recited here, but exemplary dissolvable materials include gelatin, polysaccharides, sugar, corn starch, short water-soluble inert polymers, binders, and the like, and combinations thereof.

A preferred system for isolating nucleic acids includes a unit dose form of the above dry-concentrate medium in a separate package to be used for the preparation of culture medium for culturing cells or microorganisms for the preparation of a nucleic acid to be isolated according to well known methods. Preferred are bacterial cell medium such as L-broth and the like. Exemplary media are described herein.

Thus, particularly preferred systems further include a one or more unit dose capsules, containing an amount sufficient to prepare culture medium for growing at least one sample of microorganisms for the preparation of nucleic acids to be isolated by the present invention.

A preferred system of this invention further includes instruction for use of at least one of the system components.

"Instructions for use" typically include a tangible expression describing or identifying a system component or at least one parameter for using the system such as the relative amounts of the sample and component(s) to be admixed, maintenance time periods for component/sample admixtures, temperature and the like.

The packages and containers discussed herein in relation to systems are those customarily used in the chemical arts. Such packages and containers include glass and plastic (e.g., polyethylene, polypropylene and polycarbonate) bottles, vials, tubes, plastic and plastic-foil laminated envelopes and the like.

EXAMPLES

The following examples are intended to illustrate, but not limit, the present invention. Accordingly, variations and equivalents, now known or later developed, that would be within the purview of one skilled in this art are to be considered to fall within the scope of this invention, which is limited only as set forth by the appended claims.

1. Preparation of Medium in Unit Dose Formulation

Culture medium capable of supporting growth of the bacterial cell *Escherichia coli* (*E. coli*) containing plasmid DNA was prepared by first admixing 7 gms yeast extract, 14 gms bacto-tryptone, 1.25 gms sodium chloride (all from DIFCO Laboratories, Detroit, Mi.), 0.3 gms Tris Base and 1.6 gms Tris-HCl (both Tris reagents [tris(hydroxymethyl) aminomethane] were obtained from Sigma Chemical Co., St. Louis, Mo.) to form dry concentrate medium powder, i.e., having less than 5% by weight, preferably less than 1% by weight, water.

A culture medium designated as LB-Medium (Luria-Bertani Medium) was also separately prepared by admixing 10 gms tryptone, 5 gms yeast extract, 10 gms sodium chloride, and a small amount of sodium hydroxide sufficient to form a medium having a pH of approximately 7.0 when reconstituted into a liquid medium. The powders are mixed, milled in a ball mill to a consistent 300 mesh size or smaller for admixture into a one liter medium formulation. The ingredients are available from a variety of sources such as DIFCO Laboratories, or BBL (Becton-Dickinson).

The resulting powder admixture was packaged into either a 00 or 000 size gelatin capsule using manual or automated capsule-filling machinery. A 00 size capsule will hold about 0.7 gms of LB medium, and a 000 capsule will hold about 1 gms of LB medium. Due to the hygroscopic nature of the medium ingredients, it is important that the admixing of powdered reagents, and addition to capsules be conducted in an environment having relative humidity of less that 10%. To achieve this degree of humidity, it may be necessary to utilize air conditioners that are outfitted with dehumidifiers, and allow the dehumidifiers to form a relatively dry environment.

The medium powder was packaged into unit dose amounts by placing 1 gms of the medium powder into a size 00 clear gelatin capsule (CAPSUGEL, Warner Lambert, Greenwood, S.C.) to form medium capsules. The medium may alternatively contain binders for the powdered formulations.

Two medium capsules were admixed with 50 milliliters (mls) distilled water (dH20) and subjected to a standard autoclave procedure to sterilize the liquid admixture. After autoclaving and an additional time of about 15 minutes for the autoclaved admixture to reduce in temperature, ampicillin was added to a concentration of 50 micrograms (mg) per ml to form a unitary culture medium.

*E. Coli* bacteria strain DH1 containing plasmid pUC18 (obtainable from Bethesda Research Laboratories, Gaithersburg, Md.) were inoculated into the 50 mls of unitary culture medium and the inoculated culture was maintained at 37° C. with moderate aeration for about 16 hours to form a saturated bacterial culture. The saturated culture can then be used as a source of the nucleic acids contained in the cells of the culture.

2. Additional Media Formulations

Additional media formulations are contemplated for use according to the present invention in unit dose form as described herein these formulations each are formulated for particular growth conditions and formulated for ease of use in unit dose.

For growth of plasmids in host bacterial cells a preferred medium contains, when reconstituted per liter of water: 10 gms tryptone (bacto-tryptone), 7 gms yeast extract, 7 gms NaCl, 0.4 gms Tris Base and 1.6 gms Tris HCl per 26 gms total dry medium (Formulation I). A different, preferred medium for growth of plasmids according to the present invention contains, when reconstituted per liter of water: 14 gms tryptone, 9 gms yeast extract, 5 gms NaCl, 2 gms glucose, 0.4 gms Tris Base and 1.6 gms Tris HCl per 32 gms total dry medium (Formulation II). A further preferred medium for growth of plasmids according to the present invention contains, when reconstituted per liter of water: 9 gms tryptone, 5 gms yeast extract, 0.5 gms NaCl, 3 gms casamino acids, 2 gms glucose and 0.5 gms Trizma pH 7-9 (Sigma Chemical Co.) per 20 gms total dry medium (Formulation III).

For growth of filamentous bacteriophage such as M13 in host *E. coli* bacterial cells, a preferred medium contains, when reconstituted per liter of water: 5 gms tryptone, 7 gms yeast extract, 2.5 gms NaCl, 2 gms casamino acids, and 0.5 gms Trizma pH 7-9 per 17 gms total dry medium (Formulation IV).

For growth of lambda bacteriophage in host *E. coli* bacterial cells, a preferred medium contains, when reconstituted per liter of water: 16 gms tryptone, 12 gms yeast extract, 2.5 gms NaCl, 2 gms MgSO4, 2 gms casamino acids, and 0.5 gms Trizma pH 7-9 per 35 gms total dry medium (Formulation V).

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A dry-concentrate culture medium composition in unit dose comprising an amount of cell culture medium in dry-concentrate form sufficient to prepare a preselected amount of culture medium, said dry medium packaged in unit dose form and consisting essentially of 7 grams (gms) yeast extract, 14 gms bacto-tryptone, 1.25 gms sodium chloride, 0.3 gms base and 1.6 gms-HCl per 24.15 gms total dry medium.

2. The composition of claim 1 wherein said unit dose packaging is in the form of a capsule containing said dry culture medium.

3. The composition of claim 2 wherein said capsule contains 1.0 gms of dry medium.

4. The composition of claim 1 wherein said unit dose packaging is dissolvable.

5. The composition of claim 1 wherein said dry medium has less than 5% water by weight.

6. The composition of claim 1 wherein said dry medium has less than 1% water by weight.

7. A dry-concentrate culture medium composition in unit dose comprising an amount of cell culture medium in dry-concentrate form sufficient to prepare a preselected amount of culture medium, said dry medium packaged in unit dose form and consisting essentially of 5 gms yeast extract, 10 gms bacto-tryptone, 10 gms sodium chloride and trace sodium hydroxide per 25 gms total dry medium, where said sodium hydroxide is present in an amount sufficient to produce a liquid medium of pH 7.0 when said dry medium is reconstituted at a ratio of 4 gms dry medium per 100 milliliters reconstituted medium.

8. The composition of claim 7 wherein said unit dose packaging is in the form of a capsule containing said dry culture medium.

9. The composition of claim 8 wherein said capsule contains 1.0 gms of dry medium.

10. The composition of claim 7 wherein said unit dose packaging is dissolvable.

11. The composition of claim 7 wherein said dry medium has less than 5% water by weight.

12. The composition of claim 7 wherein said dry medium has less than 1% water by weight.

13. A dry-concentrate culture medium composition in unit dose comprising an amount of cell culture medium in dry-concentrate form sufficient to prepare a preselected amount of culture medium, said dry medium packaged in unit dose form and consisting essentially of a formulation selected from the group consisting of:

Formulation I
   10 gms tryptone (bacto-tryptone),
   7 gms yeast extract,
   7 gms NaCl,
   0.4 gms Tris Base, and
   1.6 gms Tris HCl per 26 gms total dry medium;

Formulation II
   14 gms tryptone,
   9 gms yeast extract,
   5 gms NaCl,
   2 gms glucose,
   0.4 gms Tris Base, and
   1.6 gms Tris HCl per 32 gms total dry medium;

Formulation III
   9 gms tryptone,
   5 gms yeast extract,
   0.5 gms NaCl,
   3 gms casamino acids,
   2 gms glucose, and
   0.5 gms Trizma pH 7–9 per 20 gms total dry medium;

Formulation IV
   5 gms tryptone,
   7 gms yeast extract,
   2.5 gms NaCl,
   2 gms casamino acids, and
   0.5 gms Trizma pH 7–9 per 17 gms total dry medium; and Formulation V
   16 gms tryptone,
   12 gms yeast extract,
   2.5 gms NaCl,
   2 gms $MgSO_4$,
   2 gms casamino acids, and
   0.5 gms Trizma pH 7–9 per 35 gms total dry medium.

14. The composition of claim 13 wherein said unit dose packaging is in the form of a capsule containing said dry culture medium.

15. The composition of claim 14 wherein said capsule contains 1.0 gms of dry medium.

16. The composition of claim 13 wherein said unit dose packaging is dissolvable.

17. The composition of claim 13 wherein said dry medium has less than 5% water by weight.

18. The composition of claim 17 wherein said dry medium has less than 1% water by weight.

* * * * *